United States Patent [19]

Kuniyuki

[11] Patent Number: 5,279,942

[45] Date of Patent: * Jan. 18, 1994

[54] DETECTION OF PREGNANCY BY IDENTIFICATION OF THE C PEPTIDE OF RELAXIN IN BODY FLUIDS OF ANIMALS

[75] Inventor: Andrew H. Kuniyuki, Berwyn, Pa.

[73] Assignee: International Canine Genetics, Inc., Malvern, Pa.

[*] Notice: The portion of the term of this patent subsequent to Feb. 18, 2009 has been disclaimed.

[21] Appl. No.: 834,338

[22] PCT Filed: Aug. 3, 1990

[86] PCT No.: PCT/US90/04385

§ 371 Date: Feb. 6, 1992

§ 102(e) Date: Feb. 6, 1992

[87] PCT Pub. No.: WO91/02251

PCT Pub. Date: Feb. 21, 1991

Related U.S. Application Data

[63] Continuation-in-part of Ser. No. 390,626, Aug. 7, 1989, Pat. No. 5,089,419.

[51] Int. Cl.$^5$ ............... G01N 33/535; G01N 33/577
[52] U.S. Cl. .................................. 435/7.9; 436/518; 436/540; 436/548; 436/814
[58] Field of Search ............ 435/7.9, 21, 28, 810; 436/536, 547, 548, 65, 814, 510, 518; 530/387.9, 388.24, 389.1, 389.2

[56] References Cited

U.S. PATENT DOCUMENTS 4,758,516 7/1988 Hudson et al. .................. 435/253
5,089,419 2/1992 Kuniyuki .......................... 435/65

FOREIGN PATENT DOCUMENTS 86649 8/1983 European Pat. Off. .
101309 2/1984 European Pat. Off. .
303033 2/1989 European Pat. Off. .
3236267 4/1984 Fed. Rep. of Germany .

OTHER PUBLICATIONS

W. Bodsch et al., Fresenius Z. Anal. Chem., 301:133–134 (1980).
M. A. Innis et al., Proc. Natl. Acad. Sci. U.S.A, 85:9436–9440 (1988).
B. E. Kemp et al., Vitamins and Hormones, 41:79–115 (1984).
E. M. O'Byrne et al., Proc. Soc. Exp. Biol. and Med., 152:272–276 (1976).
V. Sakbun et al., J. Clin. Endocrinol. Metab., 65:339–343 (1987).
O. D. Sherwood et al., Endocrinology, 96:1106–1113 (1975).
B. G. Steinetz et al., Biol. Reproduct., 37:719–725 (1987) [Steinetz I].
B. G. Steinetz et al., Am. J. Vet. Res., 50:68–71 (1989) [Steinetz II].
L. Tashima et al., J. Encodrinol., 118:R9–R11 (1988).
U. Fuchs et al., Arch. Gynecol., 237 (Suppl.):383 (1985).
D. R. Stewart et al., Biol. Reproduction, 32:848–854 (1985).
J. Quagliarello et al., Obstetrics & Gynecology, 53(1):62–63 (1979).
P. J. Hudson et al., Chemical Abstracts, 100 (23):150 (1984).
M. Oellerich, J. Clin. Chem. Clin. Biochem., 22:895–904 (1984).

Primary Examiner—Esther L. Kepplinger
Assistant Examiner—Lora Marie Green
Attorney, Agent, or Firm—Howson and Howson

[57] ABSTRACT

The invention provides a process and products for the detection of the C peptide of relaxin in the body fluids of animals, as a positive indication of pregnancy. The invention may employ monoclonal antibodies generated to various epitopes on the C peptide.

14 Claims, No Drawings

DETECTION OF PREGNANCY BY IDENTIFICATION OF THE C PEPTIDE OF RELAXIN IN BODY FLUIDS OF ANIMALS

This is a continuation-in-part of application Ser. No. 07/390,626, filed Aug. 7, 1989, now U.S. Pat. No. 5,089,419.

The present invention relates generally to processes and products enabling the detection of pregnancy in animals. More specifically, the present invention relates to an assay for pregnancy in an animal which involves the detection and/or the qualitative measurement in body fluids of the presence of the connecting (or C) peptide of the hormone, relaxin.

BACKGROUND OF THE INVENTION

The peptide hormone, relaxin, is a pregnancy-associated polypeptide, which is present in some analogous form in most mammalian species, including human, porcine, equine, canine, rodent and feline. The relaxin molecule is processed in the body as a single prepropolypeptide containing a signal peptide, followed by a B chain, which is connected by a connecting peptide (C peptide) to an A chain. During processing the signal peptide and the C peptide are removed from the relaxin molecule. Thus the biologically active relaxin molecule present in the serum is formed of the A and B chains paired by disulfide bonds into an appropriately folded and active polypeptide.

Immunoreactivity of relaxin requires native conformation [B. E. Kemp et al., *Vitamins and Hormones*, 41:79-115 (1984)]. When the disulfide bonds of the 6300 dalton di-peptide are reduced, immunoreactivity is lost. Similarly, it is difficult to synthesize an active or immunoreactive relaxin due to the need to properly align the two interchain and one intrachain disulfides, even when a portion of the B-chain carboxy terminus is deleted to improve its solubility properties [B. E. Kemp et al., cited above].

The amino acid sequences of the prepropolypeptide of relaxin in porcine, rat and human are known and published in, for example, Bruce E. Kemp and Hugh D. Nile, Vitamins and Hormones, Vol. 41, pp. 79-115 (1984). A variety of mammalian species of relaxin and its prepropolypeptide forms demonstrate highly conserved genetic regions. The C peptide of relaxin is a larger sequence than the relaxin polypeptide itself. Because the C peptide is not itself a hormone, it is not as sensitive to degradation in the excretory or other systems.

Relaxin has been inconsistently reported in some instances as detectable in urine and in other instances as not detectable. See, e.g., West German patent application No. 3236267, published Apr. 5, 1984 which discusses a purification technique for the recovery of relaxin from urine; and U. Fuchs et al., "Presence of Immunoreactive Relaxin in Human Female Urine", *Arch. Gynecol.* 237 (Suppl.): 383 (1985). Relaxin may be denatured or degraded before being excreted and, as such, lose its immunoreactivity. Without these disulfide bonds it is probable that the relaxin molecule loses its antigenicity, if it is in fact present in urine.

The presence of relaxin in serum is presently the only good early indicator of true pregnancy in dogs [B. G. Steinetz et al., *Biol. Reproduct.*, 37:719-725 (1987) (Steinetz I); and B. G. Steinetz et al., *Am. J. Vet. Res.*, 50:68-71 (1989) (Steinetz II)]. Currently, canine serum relaxin is measured with a radioimmunoassay (RIA) over a three day protocol [E. M. O'Byrne et al., *Proc. Soc. Exo. Biol. and Med.*, 152:272-276 (1976); and O. D. Sherwood et al., *Endocrinology*, 96:1106-1113 (1975)]. Pregnancy is indicated upon observation of detectable amounts of relaxin, usually observed in pregnant dogs around the twenty-eighth day after the luteinizing hormone (LH) peak (day zero). The serum relaxin RIA test, however, still requires the help of a veterinarian or trained technician to draw blood samples.

Problems remain with utilizing this assay as a convenient method of pregnancy detection in animals. For example, serum diagnosis of pregnancy in animals is simply impractical as a means for the animals'owner or breeder to routinely practice. There is a need for reliable pregnancy detection methods because certain animals, particularly dogs, often show overt symptoms of pseudopregnancy indistinguishable from the symptoms of actual pregnancy.

Thus there remains a need in the art for convenient means for detection of the condition of pregnancy in animals, particularly for domestic animals such as dogs and cats.

SUMMARY OF THE INVENTION

The present invention meets the perceived need in the art by providing a method for diagnosis of pregnancy in animals, which encompasses the detection in body fluids of the C peptide of relaxin. The ability to detect the presence of this peptide in body fluids enables rapid, convenient and reliable pregnancy detection. At the present time, however, urine comprises the preferred mode because of the non-invasive nature of collection techniques.

As one aspect, the present invention provides a method for detecting pregnancy in an animal which involves identifying the presence in body fluids of the C peptide of relaxin. According to this invention a sample of a selected body fluid from the animal is contacted with an antibody capable of binding to an antigenic site on the C peptide of the animal. Preferably this method is applied to detection of pregnancy in domestic animals, such as dogs and cats. However, this assay may also have utility in detection of pregnancy in other animals, including, e.g., horse, cattle.

The antibody for use in the method of this invention may be a polyclonal antibody, polyclonal antisera, or, most preferably, a monoclonal antibody Presently preferred antibodies for use in this assay are capable of binding both to a site on the C peptide of the tested animal and to a contiguous sequence of rat C peptide, which contains regions of genetic conservation with other species C peptide.

In one embodiment of the method of this invention the label associated with the antibody is capable of visual detection. Preferable labels may include enzyme systems capable of generating colorimetric signals, such as horseradish peroxidase (HRP) and tetramethylbenzidine (TMB) or alkaline phosphatase and indoxyl phosphate, or systems generating visible agglutinations.

In a further aspect of this invention, the method for detecting C peptide in body fluids includes contacting the sample with two or more different labelled antibodies. In this embodiment, each antibody is capable of binding to a different epitope on the C peptide of the animal tested, and is further capable of binding to the C peptide without sterically hindering the binding of the other antibodies.

Preferably the first antibody in this method is conjugated to a first label, the second antibody is conjugated to a second label, and so on. The proximity of these enzymes upon attachment to the C peptide in the assay creates a visually detectable signal However, other detectable label systems may also be employed in this embodiment of the invention.

Still a further aspect of the present invention is an antibody capable of binding to a site on the selected animal's C peptide and to a contiguous sequence of rat C peptide, which contains regions of genetic conservation with other species C peptide. Preferably the C peptides involved are those of the canine and feline species. While such antibodies are preferably monoclonal, polyclonal antibodies and antisera sharing the same characteristics are also included in this invention. In another embodiment, these antibodies are associated with detectable labels.

A further aspect of this invention is a diagnostic kit for the detection of pregnancy in an animal, preferably a canine or feline, comprising an antibody capable of binding to the C peptide of relaxin present in the body fluids of the animal The antibody in the kit is conjugated to a detectable label. The specific antibodies described herein may also be parts of such a diagnostic kit, as well as typical buffering, washing and other diagnostic reagents conventional in such kits. Conventional components such as means for holding the sample, vials and the like are also included.

Other aspects and advantages of the present invention are described further in the following detailed description of preferred embodiments of the present invention.

DETAILED DESCRIPTION OF THE INVENTION

The present invention involves the detection of the C peptide of relaxin in body fluids as a method for identifying pregnancy in an animal, particularly a domestic animal, such as a dog or cat. This invention responds to a need in the field of breeding such animals, as well as provides a simple test for use by the owner's of animals. The method and products provided by this invention have a number of advantages in contrast to present methods for pregnancy detection of animals.

The term "body fluids" includes, but is not limited to, tears, saliva, vaginal secretions, serum, and urine. However, because of nonintrusive means of collection and the possibility of increased sensitivity, urine is the presently preferred fluid for use in this invention. Although hereafter all references to the selected animal will refer to dogs, for simplicity, it should be understood that the assays taught by the present invention may also be applied to pregnancy detection in cats, and other animals, where desirable.

One of the most obvious advantages of this invention is that, in a preferred embodiment of the present invention, detection of a substance in a body fluid such as urine, tears or saliva as opposed to substances which must be obtained from serum, e.g. the relaxin hormone, are clearly advantageous both for at home use by non-veterinarian or non-medical persons as well as for clinical use because the collection of urine, tears or saliva does not involve an invasive procedure. Thus the method and products associated therewith may be easily used by persons having no special clinical training. The presently available pregnancy tests for certain animals, particularly dogs and cats, require the intercession of a veterinarian.

Another advantage of the present invention is that practice of the present invention may allow detection of the C peptide in the body fluids of pregnant dogs earlier than the four week stage at which the intact molecule relaxin is capable of detection in the serum. This is believed to be possible because the C peptide is apparently not degraded or digested in urine or in serum. It therefore provides a larger number of binding sites for the attachment of multiple antibodies. The assays of this invention, developed to detect the C peptide in body fluids, particularly urine, may thus employ a larger number of antibodies directed to different epitopes on the C peptide. This aspect of the C peptide thus enables the use of sandwich assays, among others, which are characterized by increased sensitivity to detection of the presence of C peptide in the urine. It is believed that these advantages are similarly offered by other body fluids such as saliva, vaginal secretions, and tears.

Additionally, detection in serum of the C peptide of relaxin specifically, is believed to offer advantages over prior art methods which rely on the detection of the entire relaxin hormone Because the hormone relaxin is known to change physical characteristics within serum, it has proved difficult to design an accurate, reliable method of detection for the hormone. The present invention offers the advantage of being specifically designed to detect a stable peptide and thus provide a more accurate assay. Further, because the C peptide is not a hormone, it is not as sensitive to degradation as is the relaxin polypeptide itself.

In a preferred embodiment, the present invention deals primarily with an assay for pregnancy detection which involves identification of the presence of the C peptide in a sample taken from the body fluids of an animal.

In an assay of the invention, the fluid sample is contacted with an antibody directed to a antigenic site in the sequence of the C peptide of the dog. Such antibodies may be polyclonal antibodies, such as the illustrative antibody used in Example 1, which is a rabbit, anti-human C peptide antibody Polyclonal sera and polyclonal antibodies directed to the C peptide may be developed by conventional means.

Preferably, however, the assays of this invention will employ monoclonal antibodies (Mabs), which are known to have greater specificity to their target. Hereafter in the discussion of this invention, the term Mabs will be employed for convenience However, it is understood that polyclonal antibodies may be substituted therefor in any selected assay. Monoclonal antibodies for use in this invention will be directed to epitopes on the C peptide of the dogs. More desirably such Mabs will be employed which bind to different sites on the C peptide, so that more than one type of Mab can be employed in an assay to increase the sensitivity of the assay. Specific Mabs are developed to sequences in the C peptide which have been shown to be conserved among rat, human and porcine species. These Mabs are described in detail in Example 2 below. Briefly described, these antibodies are capable of binding to rat C peptide sequences selected from among peptides characterized by substantially the same sequences (or fragments thereof) as follows:

PHE-ILE-ASN-LYS-ASP-ALA-GLU-PRO-PHE;

ASN-LEU-SER-GLU-GLU-ARG-LYS-ALA-
ALA-LEU-SER;

ASN-GLN-LEU-GLY-GLU-ALA-GLU-ASP-
GLY-GLY-PRO-PRO-GLU-LEU-LYS-TYR;

or

GLU-LEU-LYS-TYR-LEU-GLY-SER-ASP-ALA-
GLN-SER-ARG-LYS-LYS-ARG.

It is understood by one skilled in the art that although the peptides above were obtained from the rat relaxin C peptide sequences, other mammalian sequences may also be useful where they contain genetically conserved hydrophilic sequences of C peptide analogous to sequences on canine C peptide, and therefore, desirable as immunogens to generate Mabs for use in this invention. However, this invention is not limited by the specific Mabs described in Example 2. These Mabs are illustrative only, and conventional techniques described by Kohler and Milstein and modifications by others, may be employed by one of skill in the art to generate Mabs useful in the method and products of this invention. The only requirement for selection of the appropriate monoclonal antibody for use in the practice of this invention is that, where more than one antibody is provided, the antibodies must be selected which are capable of binding at a sufficient distance from each other on the C peptide so as to prevent steric hindrance.

In the practice of the method of this invention, a variety of assay formats may be employed which use one or more monoclonal antibodies, polyclonal antibodies and antisera capable of binding to antigenic regions on the C peptide of dogs, including those described in the examples below.

One assay according to this invention is a homogeneous enzyme immunoassay employing two Mabs directed against different epitopes on the canine C peptide. The first Mab is preferably conjugated to a first enzyme (enzyme 1). A second Mab directed against a different epitope is preferably conjugated to a second enzyme (enzyme 2) which, in proximity to enzyme 1, is capable of producing a color reaction According to this embodiment of an assay of this invention, a fluid sample from a female dog is combined in a test tube or other container with both labeled Mabs. A color appears only when the fluid sample contains C peptide, because the enzymes are brought into close proximity due to side-by-side binding of their antibody conjugates to the C peptide. The product released by enzyme 1 reaction can be utilized immediately by enzyme 2 to convert the enzyme 2 co-reactant into a colored product capable of visualization. If the two enzymes are not in close proximity, e.g., in the absence of C peptide in the sample, the second reaction does not have a sufficient concentration of product 1 to proceed in generating sufficient colored product to be visible.

Another assay format employing the antibodies of this invention is performed as follows: one antibody directed to a first selected epitope on the C peptide is conjugated by conventional means to a conventional solid matrix, such as latex beads. A second antibody directed to a second epitope on the C peptide is conjugated again by conventional means to a selected enzyme. According to this assay a sample of fluid from a female dog is incubated with the first monoclonal and the latex beads. The beads are then collected generally by trapping the beads by size or charge, and separating the beads to which C peptide from the fluid is now attached via the first antibody from the fluid sample. The second monoclonal antibody is then added to the beads and allowed to react with the C peptide bound to the first monoclonal on the beads. After an appropriate reaction time, generally 2 to 30 minutes, the beads are washed and a substrate capable of reacting with the enzyme label is added to the beads. In the presence of the substrate any of the second enzyme labelled antibody which has bound due to the presence of C peptide in the fluid sample will react with the substrate and turn the sample blue, thus providing visual indication and confirmation of pregnancy. Lack of color indicates that no C peptide was present in the fluid sample and the dog that contributed the sample is not pregnant.

An alternative assay employing two or more monoclonal antibodies to different epitopes on the C peptide include a variation of the above assay in which the solid phase matrix, e.g. latex beads, are bound to a solid surface and the fluid sample is poured over the beads. This type of assay eliminates the need for collection of the beads and separation of the fluid. Other than these modifications the remaining steps as described immediately above may be performed.

Still a further variation of a diagnostic assay employing two or more antibodies of this invention is a latex agglutination assay. Such an assay is known to one of skill in the art and may be briefly described as follows. Two or more Mabs directed to different epitopes on the C peptide are bound to different solid matrices, e.g. different latex beads. Both beads are together in solution, and the urine sample is added to the solution. Standard Brownian motion keeps the beads in solution. By controlling the concentration of the beads to the amount of fluid, in the presence of C peptide in body fluid sampled, the beads having different Mabs will form a lattice network with the C peptide. The resulting agglutination or clumps of Mabs-bound beads bound to two or more sites on the C peptides are thus capable of visualization in a conventional test tube or on a slide.

Additionally, assays may be performed which only utilize a single monoclonal antibody capable of recognizing the native C peptide in body fluids. Most preferably a classical competition assay format may be employed. Alternatively an indirect immunoassay employing one Mab to the C peptide may be employed.

Briefly described, a competition assay is performed as follows: A single Mab to the native C peptide, conjugated by conventional means to a solid matrix, such as latex beads, is reacted with one milliliter of urine for about 10 minutes. A drop (approximately 50 $\mu l$) of synthetic C peptide fragment conjugated to HRP is added and incubated for an additional 5 minutes. The beads are then collected, generally by trapping by size or charge. The beads are then separated. If native C peptide is present in the sampled body fluid from a pregnant animal, the native C peptide is now attached to the beads via the Mab. In the case of a fluid sample from a non-pregnant animal which is devoid of native C peptide, synthetic C peptide HRP conjugate is now attached via the Mab specific for the native C peptide fragment. The collection surface is washed with one ml of wash reagent and 0.2 mls of TMB/urea peroxide is added.

After 5 minutes, 0.2 ml of stop reagent is added. A blue color develops in the absence of the C peptide and, therefore, a positive test remains clear. This competition assay can also be conducted with the latex-Mab conjugated spotted on a membrane or surface of commercial devices such as those manufactured by Pall Corporation, Porex, or Bio Rad, or with the Mab spotted on a dipstick. In these cases, the fluid sample and C peptide-HRP conjugate are added in sequence following the same reaction time protocol. The dipstick incubations can be performed in a test tube.

An exemplary indirect assay employing one Mab is described as follows: 100 microliter of urine is passed through nitrocellulose membrane of 3 to 5 micron porosity. Any C peptide in the sample binds non-specifically to the membrane. After 1 minute to allow absorption binding, 0.5 ml of blocking solution is added and incubated for 2 minutes to block the remaining non-specific binding sites on the membrane. This is followed by 0.5 ml of Mab to C peptide conjugated to HRP and diluted in blocking buffer. The Mab-HRP conjugate is incubated for 10 minutes. This labelled Mab will bind to any C peptide bound to the membrane. The potential signal is amplified with goat anti-antibody IgG conjugated with HRP in a 1:1000 dilution in the blocking buffer and incubated for 5 minutes. This anti-antibody will bind to the bound Mab and thus amplify the label. The membrane is washed with wash reagent and 0.2 ml of TMB/urea peroxide is added. After 5 minutes, stop reagent is added. A blue color change indicates the presence of C peptide in the fluid sample.

These and other assay formats employing one or more Mabs are known to one of skill in the art for diagnosis of many types of conditions. Variations of these described assays may be employed in the method of this invention.

Detectable labels for attachment to the antibodies of this invention for the above described assays may also be easily selected by one skilled in the art of diagnostic assays. Labels detectable visually are preferred for use in diagnostic "at-home" kits and even in clinical applications due to the rapidity of the signal and its easy readability. Most preferred are labels which provide for colorimetric detection of the presence of the C peptide. A variety of enzyme systems have been described in the art which will operate appropriately in the above-described assays. As one example of enzyme 1 in the homogeneous assay, glucose oxidase may be employed with glucose as a substrate. Interaction between glucose and glucose oxidase releases peroxide as a product. Enzyme 2 may therefore be horseradish peroxidase, which reacts with peroxide and a hydrogen donor, such as tetramethyl benzidine (TMB), producing an oxidized TMB that is seen as a blue color.

In the assays employing colorimetric enzyme systems, such as HRP or alkaline phosphatase, the reaction should be read within approximately 5 to 15 minutes, preferably 10 minutes, to obtain an accurate result. A longer reaction time can lead to color changes induced by trace amounts of enzyme remaining on the reaction surface. Where desirable, a "stop" solution can be employed to disable the enzyme from further reaction after the above 5 to 15 minute period. It is known, for example, that sulfuric acid may be added to stop the reaction of HRP. However, the acid causes a change in color from blue to yellow.

The present invention also provides for novel "stop" solutions, for both HRP and AP, which may be used in any of the above-described assays and also included in a kit. A "stop" solution for HRP includes about 20 mM sodium azide, made in 0.25 M sodium acetate to a pH of about 5.0. About 0.2 to about 0.5 mls of this solution added to the sample containing HRP after about 10 to 15 minutes, stops further reaction of HRP, retaining the blue color or no color in the assay sample indefinitely.

A "stop" solution for AP includes 0.1 M tetrasodium ethylene diamine tetraacetic acid, adjusted to a pH of approximately 7.0 with phosphoric acid. When added to the assay sample following the 5 to 15 minute reaction time, this solution stops further reaction of AP with its substrate indoxyl phosphate, also retaining indefinitely the color, or lack thereof, indicating a positive or negative test result.

Other such proximal enzyme systems are known to those of skill in the art, including hexokinase in conjunction with glucose-6-phosphate dehydrogenase which react with ATP, glucose, and NAD+ to yield, among other products, NADH that is detected as increased absorbance at 340 nm wavelength. The loss of absorbance at 340 nm wavelength by the oxidation of NADH is another indicator of positive results in either allosteric activation using phosphofructokinase in conjunction with phosphoenol pyruvate carboxylase and substrates fructose-6-phosphate and NADH or allosteric inhibition using aspartate aminotransferase in conjunction with phosphoenol pyruvate carboxylase and substrates oxalacetate, glutamate and NADH. Also, bioluminescence or chemiluminescence can be detected using, respectively, NAD oxidoreductase with luciferase and substrates NADH and FMN or peroxidase with luminol and substrate peroxide.

Other label systems that may be utilized are detectable by other means, e.g., fluorescent compounds, radioactive compounds or elements or immunoelectrodes coated with one or several antibodies. These and other appropriate label systems are known to those of skill in the art.

The methods and Mabs described herein may be efficiently utilized in the assembly of a diagnostic kit, which may be used by pet owners and breeders. Such a diagnostic kit contains the components necessary to practice one or more of the assays described above for the detection of the C peptide of relaxin in dogs. Thus, for homogeneous assays the kit may contain a first Mab directed to a first epitope on the C peptide, which Mab is associated with a first enzyme, a vial for containing the fluid sample, and a second Mab conjugated to the second enzyme, which in proximity to the first enzyme, produces a visible substrate. Other conventional components of such diagnostic kits may also be included.

Alternatively, a kit may contain a Mab directed against C peptide bound to a solid surface and associated with a first enzyme, a different Mab associated with a second enzyme, and a sufficient amount of the substrate for the first enzyme, which, when added to the urine and Mabs, provides the reactant for the second enzyme, resulting in the color change.

For an agglutination assay kit, the Mabs directed against different epitopes on the C peptide would be provided bound to the latex beads.

Where the detectable label present in association with the antibody is designed for non-visual detection, e.g., for radioimmunoassay, the standard components necessary for this assay, e.g., controls, standards and the like are included in the kit.

In the diagnostic kits of this invention, reagents are included which define a clear cut end to the color development step, such as the stop solutions described above.

The following examples illustrate the practice of the present invention using urine as the sample body fluid, including the development of presently preferred monoclonal antibodies, and various assay methods. These examples illustrated the invention only, and are not limiting thereof. The assays may also be employed in other body fluids.

EXAMPLE 1

Diagnostic Assay for Pregnancy

According to the present invention the following assay was performed to detect the presence of the C peptide in canine urine. In the performance of this test the breed of dog employed was a beagle. The dog was approximately 8 weeks pregnant. A control dog of the same breed which was not pregnant was used to determine the efficacy of this assay.

Approximately 100 microliters of canine urine from each dog was applied to a nitrocellulose membrane device having a pore size between 3 and 5 microns. Commercial devices for such use include those manufactured by Pall Corporation and Biorad. If the dog providing the urine sample is pregnant, the C peptide in the canine urine will bind non-specifically to the nitrocellulose membrane in a fairly rapid manner. After approximately 1 minute to allow the absorption binding, a blocking solution is applied to saturate any remaining non-specific binding sites on the nitrocellulose membrane. A typical blocking solution for such use may include, in a volume of 0.5 milliliters, 1% bovine serum albumin (BSA), 10% normal goat serum, 0.1% Tween-20, 0.01% thimerosal, 0.5 M NaCl, 50 mM tris, and additional conventional antibiotics to control bacterial growth. This blocking solution is desirably buffered to a pH of approximately 7.5 with hydrochloric acid. The goat serum and BSA in the blocking solution serve to block any remaining non-specific binding sites on the membrane.

After about 2 minutes following the application of the blocking solution, an antibody specific for the C peptide may be applied onto the nitrocellulose membrane. In the performance of this particular assay the antibody used was a rabbit anti-human antibody to a 34 amino acid sequence in human C peptide, hereafter called anti-HCP34, in a dilution of 1:100 in the blocking buffer at a total volume of 0.5 milliliters. This polyclonal antibody was generated to a synthetic sequence of human C peptide and provided by Dr. G. Bryant-Greenwood, Department of Anatomy and Reproductive Biology, John Burns School of Medicine, the University of Hawaii. The reaction between the anti-C peptide antibody and any C peptide from the canine urine which is bound to the nitrocellulose is allowed to occur for approximately 10 minutes. During this time the anti-C peptide polyclonal antibody will bind to the C peptide on the nitrocellulose membrane and residual liquids with unbound antibody will diffuse through the membrane.

The membrane is then washed with approximately 1 ml of buffer described as above except containing no BSA or goat serum. A goat anti-rabbit antibody, produced by conventional methods known to one of skill in the art, and conjugated to horseradish peroxidase (HRP), approximately 1:1000 in dilution in blocking buffer, is applied to nitrocellulose membrane. If the C peptide is present in the urine sample, it binds to the nitrocellulose membrane and is present on the membrane attached to the rabbit anti-C peptide antibody. The HRP-labelled goat anti-rabbit antibody will now bind to the anti-C peptide antibody creating a typical indirect immunoassay. After 5 minutes the membrane is again washed with 1 ml of washing buffer as described above.

Approximately 0.2 ml of tetramethylbenzidene (TMB) in urea peroxide is added to the nitrocellulose membrane. In the presence of horseradish peroxidase, TMB reacts to produce a blue color easily detected visually on the nitrocellulose membrane. This color change on the membrane indicates the presence of C peptide in the urine of the tested canine.

In the assay described above a blue color was revealed for the urine of the pregnant canines, while the control canine urine did not change color on the nitrocellulose paper.

Twenty dogs were tested in this immunoassay, of which 3 were known to be pregnant. The pregnant dogs tested positive in the assay of this invention, and were confirmed pregnant by sonogram tests. These dogs subsequently whelped. Seventeen of the dogs were known non-pregnant, and tested non-pregnant in the above assay of this invention.

It is understood by one skilled in the art that this same assay may be performed by altering several of the assay parameters, e.g., by adhering the nitrocellulose membrane to a plastic matrix to create a convenient dipstick pregnancy test product. Additionally the amount of the reagents or samples can be changed, and a different detectable label system may be employed.

EXAMPLE 2

Generation of C Peptide Epitopes and Monoclonal Antibodies Thereto

In generating Mabs desirable for use in the present invention, the following amino acid sequences were selected and generated synthetically by conventional means for use as immunogens in conventional methods for generating Mabs. These sequences were selected from areas of genetic conservation among rat, human and porcine C peptide sequences [Kemp et al., cited above].

Peptides were synthesized which corresponded to amino acid residues Nos. 77–85 of the rat relaxin C peptide (numbering of amino acids corresponds to the numbering of the rat peptide in Protein Identification Resource, National Biomedical Research Foundation, Georgetown University Medical Center, 3900 Reservoir Road, N.W., Washington, D.C. 20007):

PHE-ILE-ASN-LYS-ASP-ALA-GLU-PRO-PHE.

The entire peptide fragment was synthesized, as well as smaller and slightly larger fragments, including peptides having an additional cysteine residue on the amino or carboxy terminus of the selected peptide.

Another sequence from rat relaxin C peptide selected for generation of Mabs spanned amino acid residues Nos. 94 through 104 and fragments thereof:

ASN-LEU-SER-GLU-GLU-ARG-LYS-ALA-ALA-LEU-SER.

Fragments of this entire sequence were also generated, including a number of fragments with a cysteine at either the carboxy or amino termini.

Still another sequence obtained from the rat relaxin C peptide spanned from amino acid residue No. 136–151:

ASN-GLN-LEU-GLY-GLU-ALA-GLU-ASP-
GLY-GLY-PRO-PRO-GLU-LEU-LYS-TYR.

Fragments of this entire sequence, including fragments from amino acid residue Nos. 138–145, optionally containing a cysteine added to the carboxy or amino termini, were also generated.

Finally for the purposes of this example another sequence of rat relaxin C peptide from amino acid residue No. 148 through the final amino acid residue No. 162 were generated:

GLU-LEU-LYS-TYR-LEU-GLY-SER-ASP-ALA-
GLN-SER-ARG-LYS-LYS-ARG.

Smaller and larger fragments of this sequence were also generated, optionally containing a carboxy or amino terminal cysteine.

The above-described peptides or contiguous portions thereof were generated by solid phase synthesis using a polyamide resin. See, e.g. the method of Merrifield as reported in the Journal of American Chemical Society, 85:2149–2154 (1963), involving the stepwise addition of protected amino acids to a growing peptide chain which was bound by covalent bonds to a solid resin particle Reagents and byproducts are removed from this solid phase synthesis by filtration. The general concept of this method depends on attachment of the first amino acid of the chain to a solid polymer by a covalent bond and the addition of succeeding amino acids one at a time in a stepwise manner until the desired sequence is assembled.

The amino acids may be attached to any suitable polymer which merely has to be insoluble in the solvents used and have a stable physical form permitting ready filtration. The resin or matrix must also contain a functional group to which the first protected amino acid can be firmly linked by a covalent bond. Various polymers are suitable for this purpose including polyamide resins, polystyrene and polymethylmethacrylate. See, also, for example, Bodansky et al., Peptide Synthesis, Interscience, second edition (1976). As described below, the peptide may optionally be removed from the solid support and protecting groups removed.

The cysteines which are optionally attached at the carboxy or amino termini of the selected fragment provide a sulfhydryl group which may be used to link the selected peptide to a carrier protein for antibody generation or alternatively to an enzyme or other detectable label. In the generation of antibodies it is well known that small peptides become more antigenic when attached to a carrier such as a latex, keyhole limpet hemocyanin or bovine thyroglobulin.

The Mabs useful in the present invention are desirably generated in standard laboratory mice using the now traditional Kohler and Milstein techniques as well as other modifications thereof known to one of skill in the art for the generation of Mabs. Desirably, mice are injected with the selected peptide coupled to the solid phase polyamide resin or attached to a carrier protein. The mice may be sequentially boosted with the same peptide attached to different carriers to stimulate the cells to recognize the selected peptide as the target.

In the generation of Mabs for use in the following examples, two monoclonal antibody regimens are followed. In one regimen, the mice are boosted every other day for approximately 3 weeks to obtain Mabs directed to the selected peptide. Alternatively, to obtain higher affinity Mabs the mice are boosted approximately every two weeks for between 3 to 6 months to generate antibodies selected to the peptides presented.

The Mabs generated according to this example are capable of binding selectively to epitopes on the C peptide of canines felines, which are homologous to the conserved region in the rat relaxin C peptide and human relaxin C peptides. This battery of Mabs directed to the selected epitopes are useful in identifying and binding to epitopes on the canine or feline C peptides for use in assays employing one, or desirably, multiple antibody binding sites to enhance the detection of the label.

For use in these assays the label is desirably attached to the Mab by conventional methods known to one of skill in the art. For example, a presently preferred method to attach an enzyme label (horseradish peroxidase or alkaline phosphatase) to the Mab uses the heterobifunctional conjugation agent, sulfosuccinimidyl 4-(N-maleimidomethyl)cyclohexane-1-carboxylate, (SMCC). 4 mg of Mab are equilibrated in 0.1 M sodium phosphate buffer, pH 6.0 by chromatography through an excellulose column (manufactured by Pierce). Fractions containing the Mab are concentrated to 0.45 ml in a centricon 10 (manufactured by Amicon) by centrifugal concentration. 50 $\mu$l of 0.1 M 2-mercaptoethylamine in 0.1 M sodium phosphate buffer, pH 6.0 are added and incubated for 1.5 hours at 37° C. The reduced Mab is then equilibrated in 0.1 M sodium phosphate, 5 mM EDTA, pH 6.0 through excellulose chromatography and concentrated to 0.5 ml in a centricon 10. 4 mg of horseradish peroxidase are equilibrated in 50 mM sodium borate, pH 7.6 by chromatography through an excellulose column. Fractions containing the horseradish peroxidase are concentrated to 0.5 ml by centrifugal concentration in a centricon 10. 1 mg of SMCC is added and incubated for 30 to 60 minutes at 30° C. The SMCC labelled horseradish peroxidase is then equilibrated in 0.1 M Tris buffer, pH 7.0 through excellulose chromatography and concentrated to 1 ml using a centricon 10. The SMCC labelled horseradish peroxidase is then combined with the reduced Mab and incubated for 20 hours at 4° C. 10 $\mu$l of 0.1 M 2-mercaptoethylamine in 0.1 M sodium phosphate, pH 6.0 is added and incubated for 20 minutes at room temperature. The Mab horseradish peroxidase conjugate is fractionated through Sephadex G-200 chromatography in 0.15 M sodium chloride, 10 mM Tris, 0.01% thimerosal, pH 7.5 and stored at 4° C.

Other conjugation methods include one- or two-step glutaraldehyde method, periodate-oxidation method, water soluble carbodiimide method, homobifunctional imidoesters, hydroxysuccinimide esters, or maleimide methods, other heterobifunctional hydroxysuccinimidyl ester, maleimide, pyridyl disulfide or active halogen reaction methods, photoreactive phenyl azide methods, and avidin-biotin methods.

EXAMPLE 3

Detection of C Peptide in Vaginal Fluid

Dipsticks, coated with C peptide monoclonal antibody, 5E10, were prepared in the following manner: Streptavidin in 0.1 M Carbonate-Bicarbonate buffer, pH 9.5, was coated on polystyrene dipsticks for 90 minutes at 37°. Dipsticks were then incubated for 90 minutes at 37° in biotinylated goat-anti-mouse IgG in 0.1 M phosphate buffered saline, pH 7.4 (PBS). The streptavidin-biotinylated goat-anti-mouse IgG bridge was then crosslinked with dimethyl pimelimidate (DMP) in 0.2

Methanolamine, pH 8.3. Next, monoclonal antibody, 5E10, was added in PBS, then crosslinked with DMP. The dipsticks are then blocked with 1% (w/v) bovine serum albumin, 5% (w/v) sucrose in PBS, and air dried.

Synthetic C peptide containing a terminal cysteinyl residue was conjugated to horseradish peroxidase (HRP) using SMCC. TMB/urea peroxide was used as the color development substrate.

The following steps were performed to assay for the presence of C peptide: The 5E10 coated dipsticks were inserted 3 inches towards the anterior vaginal region of pregnant and non-pregnant beagles, and held in place for 5 minutes. The dipsticks were then incubated for 5 minutes in 1 ml of HRP conjugated synthetic C peptide. Next, the dipsticks were rinsed for 10 seconds under a gently stream of room temperature tap water, excess water was removed by vigorous shaking, then color development proceeded for 10 minutes in 1 ml of TMB/urea peroxide. Color development was stopped by removing the dipsticks and adding 0.2 ml of 20 mM sodium azide in 0.2 sodium acetate, pH 5.0.

C peptide in the vaginal fluids of pregnant bitches saturated monoclonal antibody 5E10 binding sites. This was observed as clear color development tubes in contrast to the distinct blue results from non-pregnant bitches.

It is understood by one of skill in the art, however, that the present invention is not limited to the specific Mabs described by the examples above, since other Mabs may be easily generated by one of skill in the art according to the teachings of the present invention.

Numerous modifications and variations of the present invention are included in the above-identified specification and are expected to be obvious to one of skill in the art. For example, use of other appropriate Mabs and detectable labels are contemplated in the performance of this invention. Such modifications and alterations to the compositions and processes of the present invention are believed to be encompassed in the scope of the claims appended hereto.

What is claimed is:

1. A method for non-invasive detection of pregnancy in a mammal comprising identifying the presence of the C peptide of relaxin in a sample of body fluids selected from the group consisting of saliva, tears and vaginal secretions, said method comprising the steps of (a) contacting the sample with at least one antibody specific for an antigenic site on the C peptide; (b) incubating the mixture for a sufficient period of time and in appropriate conditions to allow complexing of the antibody and antigen in the sample; (c) detecting any complex; and (d) correlating any complex to the presence or absence of pregnancy.

2. The method according to claim 1 wherein said mammal is selected from the group consisting of canines and felines.

3. The method according to claim 1 wherein said antibody bears a detectable label.

4. The method according to claim 3 wherein said antibody is specific for a contiguous amino acid sequence containing region of genetic conservation with the C peptide of other mammalian species.

5. The method according to claim 4 wherein mammalian species is rat, and said contiguous said sequence of C peptide is selected from the group consisting of

PHE-ILE-ASN-LYS-ASP-ALA-GLU-PRO-PHE;

ASN-LEU-SER-GLU-GLU-ARG-LYS-ALA-ALA-LEU-SER;

ASN-GLN-LEU-GLY-GLU-ALA-GLU-ASP-GLY-GLY-PRO-PRO-GLU-LEU-GLY-TYR;

and

GLU-LEU-LYS-TYR-LEU-GLY-SER-ASP-ALA-GLN-SER-ARG-LYS-LYS-ARG.

6. The method according to claim 3 wherein said antibody is selected from the group consisting of polyclonal antibodies, polyclonal antisera, and a monoclonal antibody.

7. The method according to claim 3 wherein said label is capable of visual detection.

8. The method according to claim 7 wherein said label comprises an enzyme system capable of generating colorimetric signals.

9. The method according to claim 7 wherein said enzyme system is selected from the group consisting of horseradish peroxidase and TMB or alkaline phosphatase and indoxyl phosphate 10. The method according to claim 6 wherein said label is selected from among the groups consisting of fluorescent compounds, radioactive compounds or elements.

11. A method according to claim 1 wherein step (a) comprises contacting said fluid sample with two or more different labelled antibodies, each antibody specific for a different epitope on the C peptide of said mammal without sterically hindering the binding of the other antibodies.

12. The method according to claim 11 wherein the first antibody is conjugated to a first label, said second antibody is conjugated to a second label, and the proximity of the first label to the second label upon attachment to the C peptide creates a visually detectable signal.

13. The method according to claim 1 wherein step (a) comprises exposing a fluid sample to an antibody specific for said native C peptide, which antibody is bound to a solid matrix and then exposing the sample to a synthetic C peptide associated with a label, followed by washing to separate any unbound material, wherein the presence of C peptide in said body fluid is indicated by the binding the native C peptide to the bound antibody providing no detectable label, while the absence of C peptide in said fluid is indicated by the binding of the labelled synthetic C peptide to the bound antibody which results in the appearance of the detectable label.

14. The method according to claim 1 further comprising incubating the mixture step (b) with a labelled synthetic C peptide capable of complexing with the antibody in the absence of native C peptide wherein the detection of the complex between antibody and labelled synthetic C peptide indicates the absence of pregnancy in said mammal.

* * * * *